United States Patent [19]

Daily et al.

[11] Patent Number: 5,789,576
[45] Date of Patent: Aug. 4, 1998

[54] METHYLPHOSPHONATE DIMER SYNTHESIS

[75] Inventors: William J. Daily, San Diego; David Aaron Schwartz, Encinitas, both of Calif.

[73] Assignee: Genta Incorporated, San Diego, Calif.

[21] Appl. No.: 353,530

[22] Filed: Dec. 9, 1994

[51] Int. Cl.$^6$ .................................................. C07H 21/00
[52] U.S. Cl. ................. 536/25.6; 536/25.33; 536/25.34; 536/26.5; 536/26.7; 536/26.8
[58] Field of Search ...................... 536/25.6, 25.33, 536/25.34, 26.5, 26.7, 26.8

[56] References Cited

U.S. PATENT DOCUMENTS 5,166,330  11/1992  Engels et al. ..................... 536/25.34

FOREIGN PATENT DOCUMENTS 9400472  1/1994  WIPO.

OTHER PUBLICATIONS

Lesnikowski et al., Nucleic Acid Research, vol. 16, No. 24, pp. 11675–11689 (1988).

*Primary Examiner*—James O. Wilson
*Attorney, Agent, or Firm*—Knobbe, Martens Olson and Bear, LLP

[57] ABSTRACT

Processes for the stereospecific synthesis of 2',2"-bis(deoxy) di-nucleosides and for the stereoselective synthesis of 2',2"-bis(substituted) dinucleosides are provided. Also provided are activated 2'-substituted-nucleoside alkylphosphonate active esters useful in the synthesis of these dinucleosides.

30 Claims, 4 Drawing Sheets

Figure 2A: P(V) Chemistry

X = leaving group

R = H (2'-deoxy) or
    OMe (2'OMe)

Figure 2B: P(III) Chemistry

X = leaving group

Figure 3:

1 T=DMT, R$_2$=OCH$_3$, B$_1$=N6-benzoyladeninyl
2 T=DMT, R$_2$=OCH$_3$, B$_1$=N2-isobutyrylguanidinyl
3 T=DMT, R$_2$=OCH$_3$, B$_1$=N4-isobutyrylcytosinyl
4 T=DMT, R$_2$=OCH$_3$, B$_1$=uridinyl 5 T=DMT, R$_2$=OCH$_3$, Z=O,
E=1,1,1,3,3,3-hexafluoro-2-propyl,
B$_1$=N6-benzoyladenyl
6 T=DMT, R$_2$=OCH$_3$, Z=O,
E=1,1,1,3,3,3-hexafluoro-2-propyl,
B$_1$=N2-isobutyrylguanyl
7 T=DMT, R$_2$=OCH$_3$, Z=O,
E=1,1,1,3,3,3-hexafluoro-2-propyl,
B$_1$=N4-isobutyrylcytosinyl
8 T=DMT, R$_2$=OCH$_3$, Z=O,
E=1,1,1,3,3,3-hexafluoro-2-propyl,
B$_1$=uracyl

Figure 4:

METHYLPHOSPHONATE DIMER SYNTHESIS

FIELD OF INVENTION

A method for the diastereospecific synthesis of Rp- or Sp-2',2"-bis(deoxy)methylphosphonate dinucleosides is disclosed as well a method for the diastereoselective synthesis of Rp- or Sp-2',2"bis(OMe)methylphosphonate dinucleosides. Also disclosed is their modification into reagents for the solid phase synthesis of antisense oligonucleotides containing these diastereomerically pure or diastereomerically enhanced dimers.

BACKGROUND OF THE INVENTION

Many analogues of oligonucleotides designed as "antisense" reagents have been proposed, synthesized and their biophysical and biological properties have been studied (see S. T. Crooke and B. Lebleu, Antisense Research and Applications, CRC Press, 1993). T'so and Miller (P. S. Miller et al., J. Am. Chem. Soc. 93, 6657 (1971)) proposed using nucleotides linked by methylphosphonate residues in place of naturally present phosphate moieties to increase the in vivo stability and cellular uptake. Unlike phosphate groups, methyl (or alkyl) phosphonate linkages are chiral. Solid phase synthesis of methylphosphonate oligonucleotides has been reported to yield a mixture of diastereomers at each linkage. Methylphosphonate oligonucleotides reported as synthesized under strictly controlled solution phase conditions which contain methylphosphonate linkages with Rp configuration were reported to bind with greater affinity to their complementary oligonucleotide (i.e., have higher melting temperatures (Tm)) than the corresponding oligomers containing the Sp configuration (Miller et al., Biochem. 5134, (1979) and Lesnikowski et al., Nucl. Acids Res. 18, 2109 (1990)).

The determination of the absolute configuration of the methylphosphonate diastereomer (reported as the Rp configuration) which binds more tightly to its RNA and/or DNA complement has been attempted by various methods including X-ray crystallographic determination and NMR studies (Miller et al., Nucl. Acids Res. 11, 2801 (1983), Callahan et al., Proc. Natl. Acad. Sci USA, 83, 1617 (1986) and Lebedev et al., Tetrahedron 49, 1043 (1993)).

The synthesis of methylphosphonate oligonucleotides containing all-Rp or all-Sp diastereomeric methylphosphonate linkages to study their affinities for their complementary RNA or DNA targets and their antisense biological activities has been the goal of researchers for greater than a decade (Lesnikowski et al., Nucl. Acids. Res. 18, 2109 (1990) and E. Vyazovkina et al., Nucl. Acids Res. 22, 2404 (1994)). Many methods have been developed to synthesize the methylphosphonate linkage between two 2'-deoxyribonucleosides in a diastereoselective or diastereospecific manner with the overall goal of synthesizing chirally pure methylphosphonate oligonucleotides on solid support. This goal has not yet been realized.

Figure 2A:
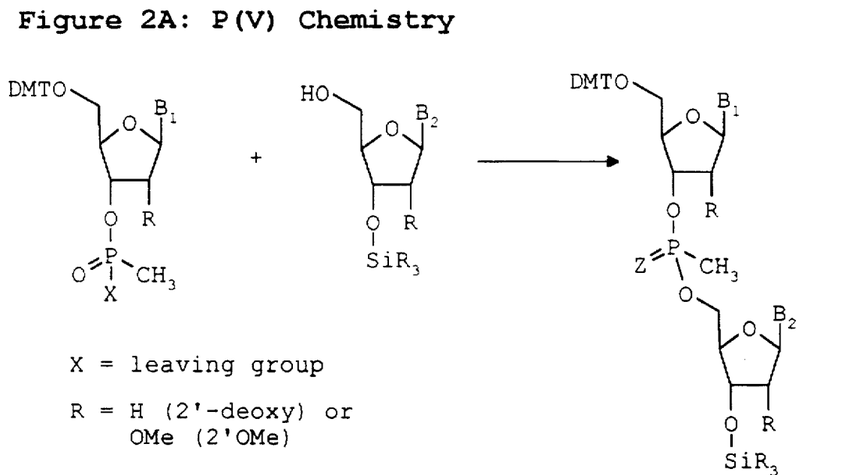
FIG. 2A depicts a scheme using P(V) chemistry.
Figure 2B:
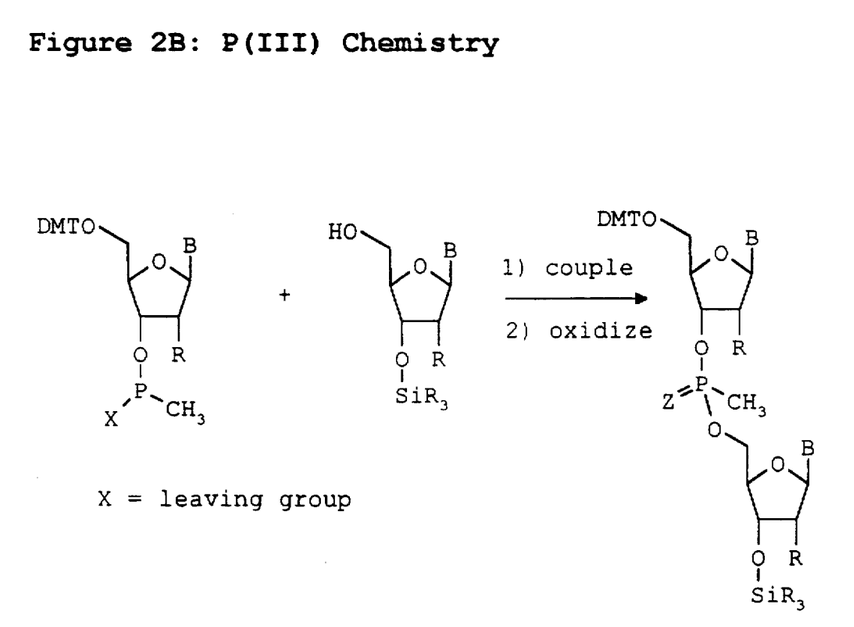
FIG. 2B depicts a scheme using P(III) chemistry.

The synthesis of a methylphosphonate dinucleoside may be accomplished by coupling of an activated 5'-O-protected-3'-O-phosphorous derivatized monomer with 5'-OH suitably protected nucleoside. This has been reported using both P(III) and P(V) chemistries (see FIG. 2). Diastereoselective methods produce mixtures of Rp- and Sp-2',2"-(bis) deoxymethylphosphonate dimers while diastereospecific methods give solely a single diastereomer. A short but not exhaustive review of some methods reported is given below. A more exhaustive review has been published recently (Lesnikowski, Bioorg. Chem. 21, 127 (1993)). All these reported methods have inadequacies as related to yield, diastereoselectivity, harshness of conditions and therefore then applicability to solid phase synthesis.

Figure 1A:
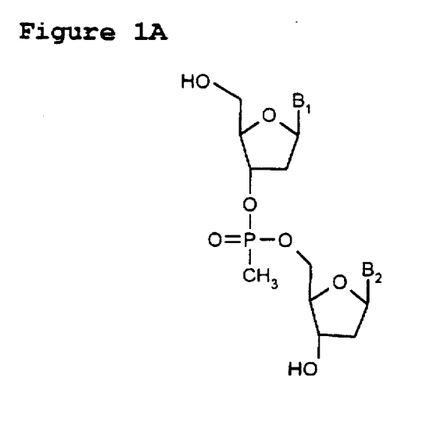
FIG. 1A depicts a 2',2"-bis(deoxy)methylphosphonate dinucleoside.
Figure 1B:
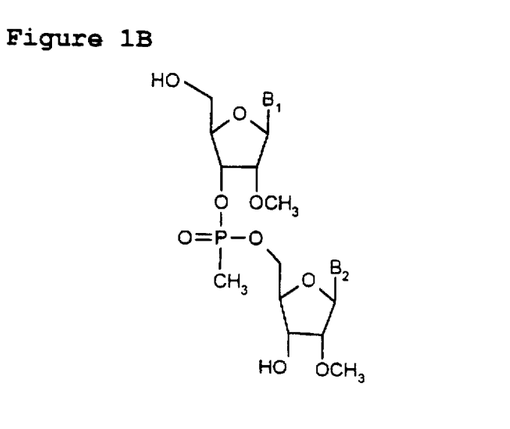
FIG. 1B a 2',2"-bis(OMe)methylphosphonate dinucleoside.

Miller et al. (Miller et al., Biochem. 30:5134 (1979)) described the syntheses of 2',2"-bis(deoxy) methylphosphonate dinucleosides (see FIG. 1 for nomenclature) using P(V) chemistry in which a 3'-O-2'-deoxymethylphosphonic acid nucleoside and a 5'-OH-2'-deoxynucleoside are condensed using triisopropylbenzenesulfonyl chloride or mesitylenesulfonyl tetrazolide but did not report the diastereomer ratio produced in the reaction.

The synthesis of methylphosphonate dinucleosides in a stereoselective manner by addition of the 5'-OH component to 1-benzotriazolyl-phosphate ester has been reported with no reference to diastereoselectivity obtained (J. E. Marugg et al., Nucl. Acids Res. 14, 2171 (1986)). C. Wang et al., Nucl. Acids Res. 21, 3245 (1993) have described the synthesis of 2'-O-TBDMS-diadenylyl methylphosphonate using the same reaction conditions as Marugg et al. and reported a 3/1 Rp/Sp diastereomeric ratio.

Engels et al. (T. Loschner and J. Engels, Tet. Lett. 5587 (1989) and W. Samstag and J. W. Engels, Angew. Chem. Int. Ed. Eng. 31, 1386 (1992)) reported the stereoselective synthesis of methylphosphonate dinucleosides. In their reports they used phosphorodichloridite chemistry to synthesize dimers. They found that the diastereomeric ratio was a factor of the nucleosides employed, base, solvent and reaction temperature.

The stereospecific synthesis of 2',2"-bis(deoxy) methylphosphonate dinucleosides has been reported by Lesnikowski et al. (Lesnikowski et al., Tet. Lett. 5535 (1987), Lesnikowski et al., Nuc. Acids Res. 16, 11675 (1988), Lesnikowski et al. Nuc. Acids. Res. 18, 2109 (1990) and Lesnikowski et al. Nucleosides Nucleotides 10 733 (1991)). Their method described the coupling of a diastereomerically pure 4-nitrophenoxymethylphosphonate ester which underwent 100% inversion of stereochemistry at the phosphorous atom when attacked by the magnesium alkoxide of an appropriately protected 5'-OH-2'-deoxynucleoside to give the diastereomerically pure 2',2"-(bis) deoxymethylphosphonate dinucleoside of inverted stereochemistry at the phosphorous atom. They found that t-BuMgCl was the optimal base for the diastereoselective synthesis of the methylphosphonate dinucleoside in pyridine. Also using t-BuMgCl, Cormier and Pannunzio (Tet. Lett. 32, 7161 (1991)) used the chirally pure 1,1,1,3,3,3-hexafluoropropanoxymethylphosphonate ester as the synthon in tetrahydrofuran solvent and demonstrated the diastereospecific synthesis of a 2'-2"-bis(deoxy) methylphosphonate dinucleoside. However, bases such as t-BuMgCl are unsuitable for use in solid phase synthesis or with certain nucleoside bases, whether protected or not.

SUMMARY OF THE INVENTION

According to one aspect, the present invention provides new milder methods for the stereospecific synthesis of 2',2"-bis(deoxy)methylphosphonate dinucleosides and the stereoselective synthesis of 2',2"-bis(OMe) methylphosphonate dinucleosides using milder conditions which do not deleteriously affect solid supports or nucleoside bases.

According to this invention, novel conditions for the stereospecific syntheses of 2',2"-bis(deoxy) methylphosphonate dinucleotides are described. In one aspect, this method uses a milder more versatile base to affect the coupling of a 5'-OH-2'-deoxy suitably protected nucleoside with a diastereomerically pure 2'-deoxymethylphosphonate active ester nucleoside than was previously described.

In a further embodiment of the invention a modification of this method was also successful in the diastereoselective synthesis of 2',2"-bis(O-methyl)methylphosphonate dinucleosides. This method is particularily advantageous since coupling 2'-O-methyl nucleosides under racemizing conditions as previously used gave high Sp/Rp ratios and it has been determined that the methylphosphonate oligonucleotides containing Rp linkages bind with much greater affinity to their RNA or DNA targets than those containing Sp diastereomers (vide supra). Also 2'-OMe substitution on the ribose of oligonucleotides has been reported to result in increased affinity (i.e. higher Tm's) for their complementary DNA and RNA targets. (See, e.g., commonly assigned U.S. patent application Ser. Nos. 08/342,924 and 08/343,018 (210/015 and 210/109) the disclosures of which are incorporated herein by reference.)

Although previous work has demonstrated that tertiary-butyl magnesium chloride effectively couples two nucleosides, t-butyl magnesium chloride is very basic (pKa>40) and very nucleophilic. These characteristics may cause unwanted interactions with nucleoside base protecting groups or unwanted side reactions with the bases. The high Ka may be incompatible with solid supports used in solid phase oligomer synthesis. We describe herein alkoxymagnesium chloride reagents which are less basic (pKa<18) and less nucleophilic however but also effectively affect the condensation of the two nucleosides. Due to the milder characteristics of the alkoxymagnesium chloride reagent, this reagent will be advantageously more compatible to other chemistries such as protecting group and solid phase chemistries than the alkylmagnesium chloride reagents.

In yet a further embodiment of this method we describe a novel high yielding synthesis of 2'-OMe methylphosphonate nucleoside active esters. Previous methods for deoxy examples (see Marugg et al.) which employed methylphosphonic acid dichloride chemistry are wont to give 3'-3'-dinucleoside methylphosphonate dimers and bis-alkoxymethylphosphonate dimers along with desired 2'-OMe methylphosphonate nucleoside active esters. According to a further aspect of the present invention, we describe a method in which a 2'-OMe phosphonamidite nucleoside is reacted with a hinded tertiary alcohol in the presence of a polar aprotic solvent, preferably tetrazole or N-ethylthiotetrazole, followed by oxidation to yield a diastereomeric mixture of the desired 2'-O-methyl methylphosphonate nucleoside active esters which can be conveniently separated by chromatography such as those procedures described herein (see FIG. 3).

Figure 4:
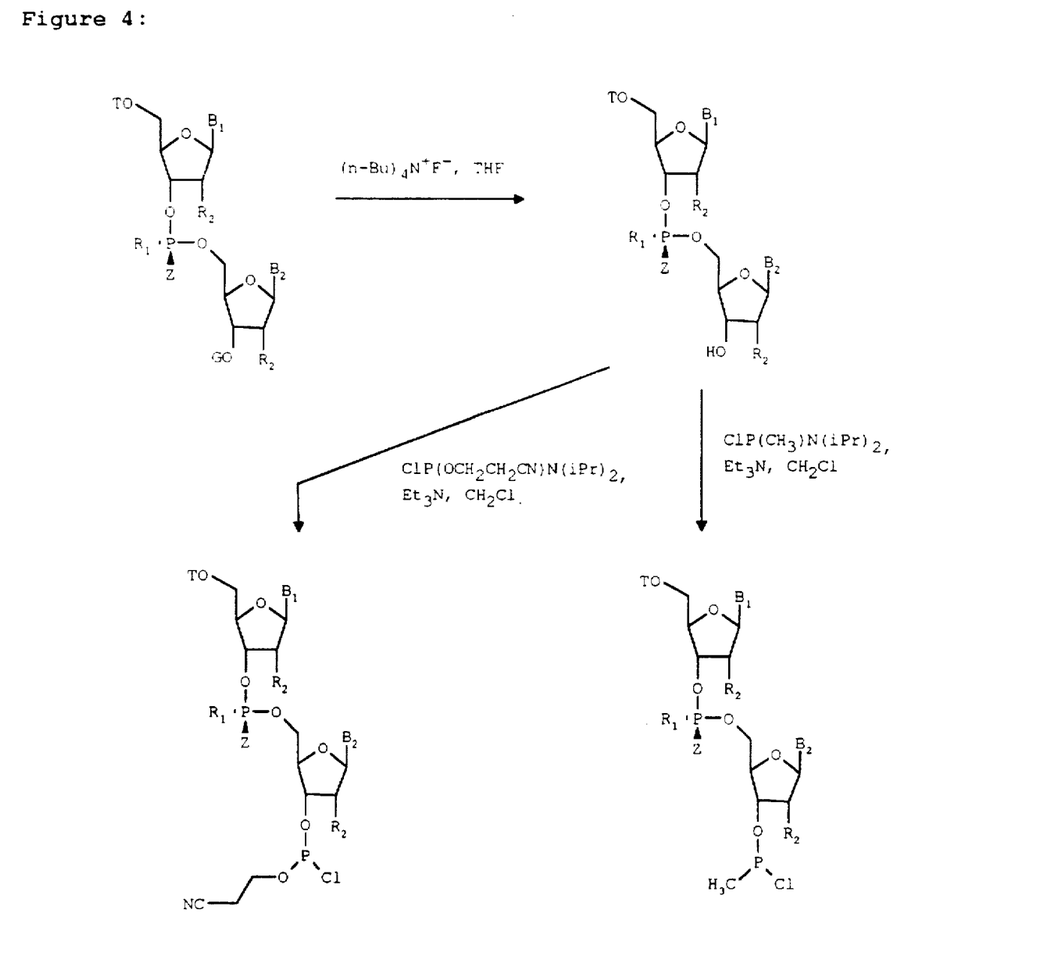
FIG. 4 depicts a scheme for conversation of diastereomerically pure methylphosphonate dinucleosides to reagents for use in solid phase synthesis of oligomers.

A further aspect of the present invention describes the modification of the 2',2"-bis(2'-OMe) dimers to give 3"-O-β-cyanoethylphoramidites or 3"-methylphosphonamidites which are useful as reagents for solid phase oligonucleotide synthesis. (See FIG. 4).

According to one aspect, the present invention provides a process for the diastereospecific preparation of 2',2"-dideoxy-diribonucleotide phosphonates of the formula 1

(1)

wherein T is an optionally substituted triphenylmethyl protecting group for a primary hydroxyl group; $B_1$ and $B_2$ are independently selected deoxyribonucleoside bases and may be the same or different; G is an acyl or silyl protecting group for a secondary hydroxyl group or a solid support; Z is selected from the group consisting of oxygen, sulfur and selenium; and $R_1$ is selected from the group consisting of an alkyl moiety having 1 to 8 carbon atoms, cyclohexyl, benzyl, phenyl and phenyl substituted by a member selected from the group consisting of fluorine, chlorine, bromine, lower alkyl, lower alkoxy and trifluoromethyl, which comprises (a) reacting an alkylmagnesium halide, with a hindered tertiary alcohol, to give a halomagnesium alkoxide;

(b) reacting the halomagnesium alkoxide with an alcohol of formula 2

(2)

; and (c) subsequently adding a diastereomerically pure Rp- or Sp- compound of general formula 3,

3 wherein E is an anion stabilizing group with leaving group properties to give the diastereomerically pure Sp-alkylphosphonate dinucleoside of formula 1 wherein stereochemistry at the phosphorus atom is inverted with respect to the stereochemistry of the configuration of the phosphorus atom of 3.

According to an alternate aspect, the present invention provides a process for the diastereoselective preparation of 2',2"-bis(substituted)diribonucleotide phosphonates of the formula 4 wherein

T is an optionally substituted triphenylmethyl protecting group for a primary hydroxyl group; $B_1$ and $B_2$ are independently selected nucleoside bases and may be the same or different; G is an acyl or silyl protecting group for a secondary hydroxyl group or a solid support; Z is selected from the group consisting of oxygen, sulfur and selenium; $R_1$ is selected from the group consisting of an alkyl moiety having 1 to 8 carbon atoms, cyclohexyl, benzyl, phenyl and phenyl substituted by a member selected from the group consisting of lower alkyl and trifluoromethyl; and $R_2$ is selected from the group consisting of hydrogen, O-alkyl of 1 to about 10 carbon atoms, O-alkenyl, O-aralkyl of 7 to about 11 carbon atoms, O-aryl of 6 to about 10 carbon atoms, halogen and nitrile; which comprises:

(a) reacting an alkylmagnesium halide, with a hindered tertiary alcohol to give a halomagnesium alkoxide;

(b) reacting the halomagnesium alkoxide of step (a) with an alcohol of general formula 5 and (c) subsequently adding a diastereomerically pure Rp- or Sp- compound of general formula 6, wherein E is an anion stabilizing group with leaving group properties to give the diastereomerically-enriched alkylphosphonate dinucleoside of formula 4, and wherein inversion of stereochemistry at the phosphorus atom of 6 is favored.

In another aspect the present invention is directed to diastereomerically pure (at P) compounds of formula 4 wherein T is selected from the group consisting of triphenylmethyl, p-anisoyldiphenylmethyl and di(p-anisoyl) phenylmethyl; $B_1$ and $B_2$ are independently selected nucleoside bases and are the same or different; $R_1$ is selected from the group consisting of methyl, ethyl, phenyl, benzyl and propynyl; $R_2$ is selected from the group consisting of O-alkyl of 1 to about 10 carbon atoms, O-alkenyl of 2 to about 10 carbon atoms, O-aralkyl of 7 to about 10 carbon atoms, O-aryl of 6 to about 10 carbon atoms, halogen and nitrile; and G is selected from the group consisting of t-butyl-dimethylsilyl, trimethylsilyl, t-butyl-diphenylsilyl, and a solid support.

A further aspect of the present invention provides a process for the preparation of racemic mixtures and diastereomerically pure 2'-substituted nucleoside alkylphosphonate active esters of the formula 6:

wherein

T is a triphenylmethyl protecting group for a primary hydroxyl group; $B_1$ is a nucleoside base; G is an acyl or silyl protecting group for a secondary hydroxyl group or a solid support; Z is selected from the group consisting of oxygen, sulfur and selenium; $R_1$ is selected from the group consisting of an alkyl moiety having 1 to 8 carbon atoms, cyclohexyl, benzyl, phenyl and phenyl substituted by a member selected from the group consisting of lower alkyl and trifluoromethyl; and $R_2$ is selected from the group consisting of hydrogen, O-alkyl of 1 to about 10 carbon atoms, alkenyl of 2 to about 10 carbon atoms, O-aralkyl of 7 to about 11 carbon atoms, O-aryl of 6 to about 10 carbon atoms, halogen and nitrile; and E is an anion stabilizing group with leaving group properties; which comprises

(a) reacting a phosphonamidite reagent of formula 7 with an alcohol of formula E-OH, in the presence of a weak organic acid in a polar aprotic solvent;

(b) oxidatively converting the P(III) intermediate to a compound of formula 6; and (c) chromatographically separating the mixture of Rp- and Sp- diastereomers formed in the reaction.

Also provided are compounds of formula 6 wherein

T is an optionally substituted triphenylmethyl protecting group for a primary hydroxyl group; $B_1$ is a nucleoside base; Z is selected from oxygen, sulfur or selenium; $R_1$ is selected from the group consisting of methyl, ethyl, phenyl, benzyl and propenyl; $R_2$ is selected from the group consisting of hydrogen, O-alkyl of 1 to about 10 carbon atoms, O-alkenyl of 1 to about 10 carbon atoms, O-aralkyl of 7 to about 10 carbon atoms, O-aryl of 6 to about 10 carbon atoms, halogen and nitrile; and E is an anion stabilizing group with leaving group properties. These compounds are conveniently separated to give either the Rp- or Sp diastereomer.

Definitions

In accordance with the present invention and as used herein, the following terms are defined to have following meanings, unless explicitly stated otherwise:

The term "alkyl" refers to saturated aliphatic groups including straight-chain, branched-chain and clyclic groups. Suitable alkyl groups include cyclohexyl and cyclohexylmethyl. "Lower alkyl" refers to alkyl groups of 1 to 6 carbon atoms.

The term "aryl" refers to aromatic groups which have at least one ring having a conjugated pi electron system and includes carbocyclic aryl, heterocyclic aryl and biaryl groups, all of which may be optionally substituted.

The term "carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carboxyclic aryl groups include phenyl and naphthyl.

The term "heterocyclic aryl" refers to aryl groups having from 1 to 3 heteroatoms as ring atoms in the aromatic ring and the remainder of the ring atoms are carbon atoms. Suitable heteroatoms include oxygen, sulfur, and nitrogen, and suitable heterocyclic aryls include furanyl, thienyl, pyridyl, pyrrolyl, pyrimidyl, pyrazinyl, imidazolyl, and the like.

The term "biaryl" refers to phenyl substituted by carbocyclic or heterocyclic aryl as defined herein, ortho, meta or para to the point of attachment of the phenyl ring, advantageously para.

The term "lower" referred to herein in connection with organic radicals or compounds defines such with up to and including 6, preferably up to and including 4 and advantageously one or two carbon atoms. Such groups may be straight chain or branched chain.

The term "alkoxyl" refers to —OR wherein R is alkyl.

The term "alkoxycarbonyl" refers to —C(O)OR wherein R is alkyl.

The term "aralkyl" refers to an alkyl group substituted with an aryl group. Suitable aralkyl groups include benzyl, picolyl, and the like, all of which may be optionally substituted.

The term "perfluoroalkyl", refers to an alkyl group which has every hydrogen replaced with fluorine.

The term "perfluoroaryl" refers to an aryl group which has every hydrogen replaced with fluorine.

The term "perfluoroaryl alkyl" refers an aralkyl group in which every hydrogen on the aryl moiety is replaced with fluorine.

The term "cycloalkyl", refers to a cyclic alkyl group. Suitable cycloalkyl groups include cyclohexyl.

The term "alkenyl" refers to an unsaturated aliphatic group having at least one double bond.

The term "aralkenyl" refers to an alkenyl group substituted with an aryl group.

The term "purine" or "purine base" includes not only the naturally occurring adenine and guanine bases, but also modifications of those bases such as bases substituted at the 8-position, or guanine analogs modified at the 6-position or the analog of adenine, 2-aminopurine, as well as analogs of purines having carbon replacing nitrogen at the 9-position such as the 9-deazapurine derivatives and other purine analogs. Also included are suitably protected purine bases such as 6-benzoyladenine and 2-isobutyrylguanine.

The term "pyrimidine" or "pyrimidine base", includes not only the naturally occurring cytosine, uracil and thymine but also modifications to these bases such as 5-propynyluracil, 5-heteroaryluracils and analogs of pyrimidine such as reported heteroaromatic moieties. Also included are suitably protected pyrimidine bases such as 4-isobutyrylcytidine.

The term "nucleoside" includes a nucleosidyl unit and is used interchangeably therewith, and refers to a subunit of a nucleic acid which comprises a 5-carbon sugar and a nitrogen-containing base. The term includes not only those nucleosidyl units having A, G, C, T and U as their bases, but also analogs and modified forms of the naturally-occurring bases, including the pyrimidine-analogs such as pseudoisocytosine and pseudouracil and other modified bases (such as 8-substituted purines). In RNA, the 5-carbon sugar is ribose; in DNA, it is a 2'-deoxyribose. The term nucleoside also includes other analogs of such subunits, including those which have modified sugars such as 2'-O-alkyl ribose.

The term "phosphonate" refers to the group wherein X is oxygen, selenium or sulfur, R is hydrogen or an alkyl or aryl group, and thus includes various example of phosphonate and phosphonothioate internucleosidyl linkages. Suitable alkyl or aryl groups include those which do not sterically hinder the phosphonate linkage or interact with each other. The phosphonate group may exist in either an "Rp" or an "Sp" configuration. Phosphonate groups may be used as internucleosidyl linkages (or links) to connect nucleosidyl unit or a nucleosidyl unit and a non-nucleosidy monomeric unit. The term "lower alkylphosphonate" refers to groups where X is oxygen and R is lower alkyl of 1 to 3 carbon atoms. "Methylphosphonate" refers to groups where X is oxygen and R is methyl. The term "phosphonothioate" refers to those groups where X is sulfur. The term "lower alkylphosphonothioate" refers to groups where X is sulfur and R is lower alkyl of 1 to 3 carbon atoms. The term "methylphosphonothioate" refers to a phosphonothioate group wherein R is methyl.

The term "phosphodiester" or "diester" refers to the group wherein phosphodiester groups may be used as internucleosidyl phosphorus group linkages (or links) to connect nucleosidyl units.

A "non-nucleoside monomeric unit" refers to a monomeric unit wherein the base, the sugar and/or the phosphorus backbone has been replaced by other chemical moieties.

A "nucleoside/non-nucleoside polymer" refers to a polymer comprised of nucleoside and non-nucleoside monomeric units.

The term "oligonucleoside" or "Oligomer" refers to a chain of nucleosides which are linked by internucleoside linkages which is generally from about 4 to about 100 nucleosides in length, but which may be greater than about 100 nucleosides in length. They are usually synthesized from nucleoside monomers, but may also be obtained by enzymatic means. Thus, the term "Oligomer" refers to a chain of oligonucleosides which have internucleosidyl linkages linking the nucleoside monomers and, thus, includes oligonucleotides, nonionic oligonucleoside alkyl- and aryl-phosphonate analogs, alkyl- and aryl-phosphonothioates, phosphorothioate or phosphorodithioate analogs of oligonucleotides, phosphoramidate analogs of oligonucleotides, neutral phosphate ester oligonucleoside analogs, such as phosphotriesters and other oligonucleoside analogs and modified oligonucleosides, and also includes nucleoside/non-nucleoside polymers. The term also includes nucleoside/non-nucleoside polymers wherein one or more of the phosphorus group linkages between monomeric units has been replaced by a non-phosphorous linkage such as a formacetal linkage, a thioformacetal linkage, a morpholino linkage, a sulfamate linkage, a silyl linkage, a carbamate linkage, an amide linkage, a guanidine linkage, a nitroxide linkage or a substituted hydrazine linkage. It also includes nucleoside/non-nucleoside polymers wherein both the sugar and the phosphorous moiety have been replaced or modified such as morpholino base analogs, or polyamide base analogs. It also includes nucleoside/non-nucleoside polymers wherein the base, the sugar, and the phosphate backbone of the non-nucleoside are either replaced by a non-nucleoside moiety or wherein a non-nucleoside moiety is inserted into the nucleoside/non-nucleoside polymer, optionally, said non-nucleoside moiety may serve to link other small molecules which may interact with target sequences or alter uptake into target cells.

The term "alkyl- or aryl-phosphonate Oligomer" refers to Oligomers having at least one alkyl- or aryl-phosphonate internucleosidyl linkage and the remainder of the internucleosidyl linkages phosphonate internucleosidyl linkages. Suitable alkyl- or aryl-phosphonate groups include alkyl- or aryl- groups which do not sterically hinder the phosphonate linkage or interact with each other. Preferred alkyl groups include lower alkyl groups having from about 1 to about 6 carbon atoms. Suitable aryl groups have at least one ring having a conjugated pi electron system and include carbocyclic aryl and heterocyclic aryl groups, which may be optionally substituted and preferably having up to about 10 carbon atoms.

The term "methylphosphonate Oligomer" (or "MP-Oligomer") refers to Oligomers having at least one methylphosphonate internucleosidyl linkage and the remainder of the internucleosidyl linkages phosphonate linkages.

The term "neutral oligomer" refers to Oligomers which have nonionic internucleosidyl linkages between nucleoside monomers (i.e., linkages having no positive or negative ionic charge) and include, for example, oligomers having internucleosidyl linkages such as alkyl- or aryl- phosphonate linkages, alkyl- or aryl-phosphonothioates, neutral phosphate ester linkages such as phosphotriester linkages, especially neutral ethyltriester linkages; and non-phosphorus-containing internucleosidyl linkages, such as sulfamate, morpholino, formacetal, thioformacetal, silyl, and carbamate linkages. Optionally, a neutral Oligomer may comprise a conjugate between an oligonucleoside or nucleoside/non-nucleoside polymer and a second molecule which comprises a conjugation partner. Such conjugation partners may comprise intercalators, alkylating agents, binding substances for cell surface receptors, lipophilic agents, nucleic acid modifying groups including photo-cross-linking agents such as psoralen and groups capable of cleaving a targeted portion of a nucleic acid, and the like. Such conjugation partners may further enhance the uptake of the Oligomer, modify the interaction of the Oligomer with the target sequence, or alter the pharmacokinetic distribution of the Oligomer. The essential requirement is that the Oligomer conjugate comprises be substantially neutral.

The term "substantially neutral" in referring to an Oligomer refers to those Oligomers in which at least about 80 percent of the internucleosidyl linkages between the nucleoside monomers are nonionic linkages.

"MP(Rp)" refers to a methylphosphonate internucleosidyl linkage of Rp chirality.

An oligomer having "alternating MP(Rp)/MP internucleosidyl linkages" refers to an Oligomer wherein methylphosphonate linkages of Rp chirality alternate with methylphosphonate linkages of undefined chirality (i.e., racemic).

A "MP(Rp)/MP dimer synthon" refers to a dinucleoside wherein the two nucleosides are linked by a mehylphosphonate internucleosidyl linkage of Rp chirality and one of the nucleosides has a 5'- or 3'- coupling group which when coupled to a 3'-OH or a 5'-OH, of another nucleoside or an oligomer will result in a methylphosphonate internucleosidyl linkage.

A "2'-O-methyl MP(Rp)/2'-O-methyl MP dimer synthon" refers to a dinucleoside wherein two 2'-O-methyl nucleosides are linked by a methylphosphonate linkage of Rp chirality and one of the nucleosides has a 5'- or 3'-coupling group which when coupled to a 3'-OH or 5'-OH of another nucleoside or an oligomer will result in a methylphosphonate internucleosidyl linkage.

An oligomer having "alternating MP(Rp)/DE internucleosidyl linkages" refers to an Oligomer wherein methylphosphonate linkages of Rp chirality alternate with phosphodiester linkages ("DE").

A "MP(Rp)/DE dimer synthon" refers to a dinucleoside wherein the two nucleosides are linked by a mehylphosphonate internucleosidyl linkage of Rp chirality and one of the nucleosides has a 5'- or 3'-coupling group which when coupled to a 3'-OH or a 5'-OH, of another nucleoside or an oligomer will result in a phosphodiester internucleosidyl linkage.

A "MP(Rp)/PS dimer synthon" refers to a dinucleoside wherein the two nucleosides are linked by a methylphosphonate linkage of Rp chirality and one of the nucleosides has a 5'- or 3'- coupling group which when coupled to a 3'-OH or 5'-OH of another nucleoside or an oligomer will result in a phosphorothioate internucleosidyl linkage.

A "MP(Rp)/PS$_2$ dimer synthon" refers to a dinucleoside wherein the two nucleosides are linked by a methylphosphonate linkage of Rp chirality and one of the nucleosides has a 5'- or 3'- coupling group which when coupled to a 3'-OH or 5'-OH of another nucleoside or an oligomer will result in a phosphorothioate internucleosidyl linkage.

A "2'-O-methyl MP(Rp)/2'-O-methyl DE dimer synthon" refers to a dinucleoside wherein two 2'-O-methyl nucleosides are linked by a methylphosphonate linkage of Rp chirality and one of the nucleosides has a 5'- or 3'-coupling group which when coupled to a 3'-OH or 5'-OH of another nucleoside or an oligomer will result in a phosphodiester internucleosidyl linkage.

FIGS. 1A and 1B depict the structures of dinucleosides made according to the methods of the present invention.

FIGS. 2A and 2B depict general schemes for the synthesis of methylphosphonate dinucleosides.

DETAILED DESCRIPTION OF THE INVENTION

As was herein above by groups, including Lesnikowski et al., activation of a suitably protected 5'-OH-nucleoside by the use of t-BuMgCl/pyridine as the base/solvent system and subsequent addition of a diastereomerically pure 3'-O-methylphosphonate active ester was reported to be their preferred method for the diastereospecific synthesis of a 2',2"-bis(deoxy)methylphosphonate dinucleosides. We have found these conditions to be suboptimal as the pKa of this base is >40 and this reagent is very nucleophilic. These properties of t-BuMgCl limit usefulness of the reported method due in part to limitations, for example, on the types of protecting groups which can be employed and the possibility of side reactions on the nucleoside. These properties would be especially troublesome when used with solid supports since the types of chemistry available for linking a nucleoside to the solid support would be limited and probability of side reactions on the growing oligonucleotide chain would increase.

We have found that alkoxymagnesium chloride bases, preferably t-BuOMgCl, 3-ethylpent-3-anoxyMgCl or adamant-1-oxyMgCl, can be used to induce coupling of a diastereomerically pure Rp- or Sp-2'-deoxy-3'-P(V)-active ester and a 2'-deoxy-5'-OH nucleoside yielding the diastereomerically pure Sp- or Rp- methylphosphonate dinucleoside respectively (see FIG. 2, R$_2$=H). Table 1 further demonstrates the utility of alkoxymagnesium chloride bases with respect to diastereospecificity and yields as compared to other bases. The Examples describe the diastereospecific syntheses of a number of 2',2"-bis(deoxy) methylphosphonate dinucleosides (Table 2) and the stereoselective syntheses of all sixteen 2',2"-bis(OMe) methylphosphonate dinucleosides (Table 3) using the methods of the present invention.

The procedure to accomplish the diastereospecific coupling of 2'-deoxyribonucleosides follows. The alkoxy Grignard reagent is readily prepared in situ by addition of t-BuMgCl to a solution of an alcohol, preferrably a hinded tertiary alcohol, preferrably selected from t-BuOH, 2-ethyl-2-pentanol or 1-adamantanol at 0° in a polar aprotic solvent such as tetrahydrofuran. The 5'-OH-3'-O-trialkylsilyl-protected (or 3'-O-solid support coupled) nucleoside is subsequently added to preform the nucleophile. The electrophilic diastereomerically pure Rp- or Sp-2'-deoxy-3'-P(V)-active ester is then added dropwise to the reaction mixture and the solution is stirred at room temperature for about 4 to about 17 hours. Work-up of the reaction mixture as outlined in Example 1 gives diastereomerically pure dinucleoside. The results of the coupling of five of the sixteen possible natural dimers in solution phase are given in Table 1.

We also describe the synthesis of 2',2"-bis(OMe) methylphosphonate dinucleosides which are synthesized in a diastereoselective manner. To this end we describe a novel synthesis of 2'-OMe-3'-O-P(V)-active esters via coupling of the 2'-OMe-phosphonamidite nucleoside and the desired alcohol in the presence of tetrazole under anhydrous conditions followed by oxidation to give a diastereomeric mixture of the desired alkylphosphonate esters in high yield (see FIG. 3 and Table 4). The diastereomers are readily separated by chromotography. Coupling of the 2'-OMe alkylphosphonate active ester with the chloroalkoxymagnesium base activated 5'-OH nucleoside requires elevated temperatures compared to the aforementioned 2'-deoxy example. The reaction temperature for the 2'-OMe case is between 15°-65° C., preferrably 55° C. for 12–66h (see Example 7). The results of the synthesis of all sixteen natural dinucleotides are give in Table 3.

The 2',2"-bis(OMe)methylphosphonate dinucleosides are further converted to solid phase synthesis-ready synthons as phosphonamidites or phosphoramidites for incorporation into oligonucleotides (see Scheme 4).

General Synthesis Procedures

All reactions were run under a positive pressure of dry argon. Reactions requiring anhydrous conditions were performed in flame-dried glassware which was cooled under argon. Anhydrous solvents and reagent solutions were transferred using oven-dried syringes.

Solvents and reagents not described as anhydrous were dried in the following manner: Tetrahydrofuran (THF) was distilled from potassium/benzophenone ketyl immediately prior to use; 3-ethyl-3-pentanol was dried over 3 Å or 4 Å molecular sieves for 24 hours prior to use. Methylene chloride, pyridine, acetonitrile, tetrazole reagent and 2-methyl-2-propanol were obtained as anhydrous reagents (<0.005% water) and were used without further purification. Reagent grade solvents were used for chromatography without further purification.

TLC was performed on 0.2 mm E. Merck precoated silica gel 60 $F_{254}$ (20×20 cm aluminum sheets). Flash chromatography was performed using E. Merck 230–400 mesh silica gel (60 $F_{254}$).

Analytical Reverse-phase HPLC was done using a Beckman Ultrasphere C-18 column, 4.6 mm×250 mm, on Beckman System Gold 126 pump systems with a Model 168 diode-array detector. The solvents used were: A-50% acetonitrile in 0.05M triethylammonium acetate (TEAA) pH 7.0–7.2; and B-100% acetonitrile. The gradient system used was 0–100% B over 20 minutes at a flow rate of 1.0 mL/min. All analytical reverse-phase chromatograms were monitored at 260 nm.

The NMR and MS data given in the examples were obtained as follows: $^1$H NMR and $^{31}$P spectra were recorded on a 300 MHz Bruker ARX 300 Spectrometer. All $^1$H and $^{31}$P were obtained in $CDCl_3$ unless otherwise indicated. FAB Mass spectra were provided by The Scripps Research Institute Mass Spectrometry Facility of San Diego, Calif. The spectra were obtained using a Cs ion gun and were recorded on a FISONS/VG-ZAB-VSE High Resolution Mass Spectrometer. All $^1$H NMR, $^{31}$P NMR, and MS spectra obtained were consistent with assigned structure.

To assist in understanding the present invention, the following examples are included which described the results of a series of experiments. The following examples relating to this invention should not, of course, be construed in specifically limiting the invention and such variations of the invention, now known or later developed, which would within the purview of one skilled in the art are considered to fall within the scope of the present invention as hereinafter claimed.

EXAMPLE 1

General Procedure for the Synthesis of 2'-Deoxy Methyl Phosphonate Dinucleotides To a flame-dried one-neck round-bottomed flask were added the metal/base reagents (THF solvent was also added as needed). A THF solution of the 2'-deoxy nucleoside 5'-OH component (1.0 equiv.) was then added at room temperature via syringe. The reaction mixture was stirred at room temperature for 20 minutes. Then, a THF solution of the 2'-deoxy nucleoside 3'-1,1,1,3,3,3-hexafluoro-2-propyl methylphosphonate component (2.0 or 1.3 equivalents, see Table 2) was added via syringe and the reaction mixture was stirred at either room temperature or 50° C. (see Table 2 for reaction temperature and duration). The reactions were quenched with saturated aqueous ammonium chloride solution and extracted with ethyl acetate. Organic extracts were washed with brine, dried ($MgSO_4$), filtered and concentrated under reduced pressure to give a yellow-orange foam. Yields of dinucleotides were generally estimated by $^{31}$P NMR integration (see Table 2). Where applicable, purification of the dinucleotide was performed by flash chromatography on silica gel using a solvent mixture composed of 75:25:3 ethyl acetate-methylene chloride-methanol, increasing to 75:25:10 ethyl acetate-methylene chloride-methanol.

EXAMPLE 2

General Procedure for the Preparation of (Rp)- and (Sp)-1,1,1,3,3,3-Hexafluoro-2-propyl 2'-O-Methyl Nucleoside 3'-Methylphosphonates To a solution of the 2'-OMe nucleoside 3'-phosphoramidite (1.0 equiv) in dry acetonitrile (4 mL per mmol of phosphoramidite) at room temperature were added via syringe 1,1,1,3,3,3-hexafluro-2-propanol (2.0 equiv) and then tetrazole reagent (0.45M solution in acetonitrile, 2 equiv). The reaction was stirred at room temperature for 3 min and then transferred to a round-bottomed flask containing $I_2$-pyridine-THF-$H_2O$ (0.1M in $I_2$, 2 equiv, prepared by dissolving 2.54 g $I_2$ in a mixture of 74.75 mL THF, 25 mL pyridine and 0.25 mL $H_2O$). The resulting mixture was stirred at room temperature for 20 minutes. The reaction was quenched by adding 10% aqueous sodium bisulfite solution and after 10 minutes the resulting bilayer was extracted with ethyl acetate. The organic extracts were washed twice with 10% aqueous citric acid solution, once with saturated aqueous sodium bicarbonate solution and once with brine. The organic extracts were dried (MgSO4), filtered and concentrated under reduced pressure to afford a pale yellow foam. The diastereomers were separated by flash chromatography on silica gel (230–400 mesh) using a mixture of methylene chloride-acetone (see compound for solvent ratio).

EXAMPLE 3

Figure 3:
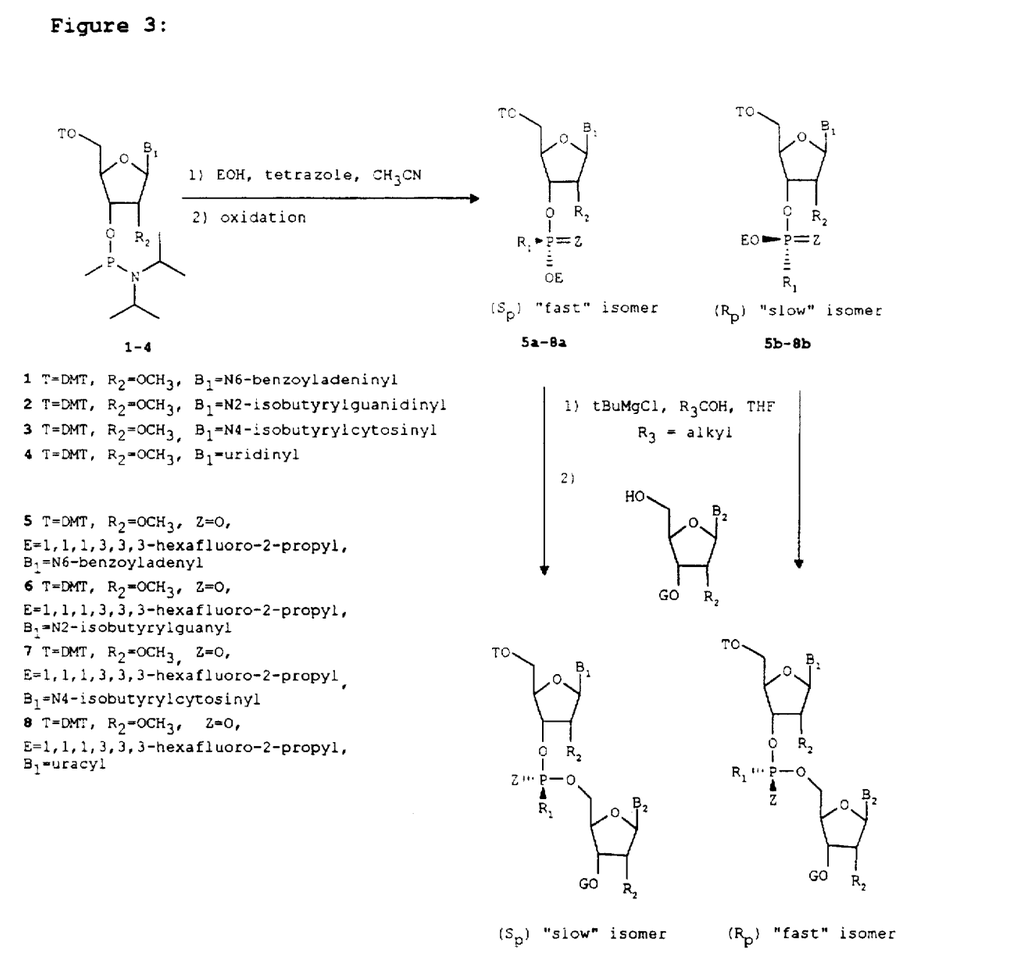
FIG. 3 depicts a scheme for synthesis of methylphosphonate dinucleosides according to the process of the present invention.

Preparation of (Rp)- and (Sp)-1,1,1,3,3,3-Hexafluoro-2-propyl $N^6$-benzoyl-5'-O-(4,4'-dimethoxytrityl)-2'-O-methyladenosine 3'-Methylphosphonate(5a,b, FIG. 3)

Following the general procedure of Example 2 with 5.55 g (6.66 mmol) of phosphonamidite 1 provided a 1:2.8 mixture (determined by $^{31}$P NMR integration) of diastereomers 5a (Sp, fast) and 5b (Rp, slow), respectively. Flash chromatography on silica gel using 6:1 methylene chloride-acetone gave 0.58 g (9%) of 5a, 1.94 g (32%) of 5b and 2.99 g (49%) of a mixture of 5a and 5b.

Diastereomer 5a: mp: 108°–110° C.; Rf 0.27 (6:1 methylene chloride-acetone); $^1$H NMR (300 MHz, $CDCl_3$) δ9.29 (br s, 1 H), 8.67 (s, 1 H), 8.16 (s, 1 H), 8.02 (d, J=7.5 Hz, 2 H), 7.60–7.41 (m, 5 H), 7.32–7.22 (m and overlapping d, J=8.7 Hz, 7 H), 6.81 (d, J=8.7 Hz, 4 H), 6.18 (d, J=6.6 Hz, 1 H), 5.37 (septet, J=6.0 Hz, 1 H), 5.26 (ddd, J=8.7, 4.8, 2.7 Hz, 1 H), 4.89 (t, J=5.4 Hz, 1 H), 4.51 (d, J=2.70 Hz, 1 H), 3.77 (s, 6 H), 3.56 (dd, J=10.8, 3.9 Hz, 1 H), 3.46–3.41 (s, 3 H and overlapping dd, J=10.8, 3.6 Hz, 1 H), 1.71 (d, J=18.0 Hz, 3 H); $^{31}$P NMR (121 MHz, $CDCl_3$) δ34.10; HRMS (FAB$^+$) calcd for $C_{43}H_{40}F_6N_5O_9P$+H 916.2546, found 916.2569.

Diastereomer 5b: mp: 112°–114° C.; Rf 0.18 (6:1 methylene chloride-acetone); $^1$H NMR (300 MHz, $CDCl_3$) δ9.08 (s, 1 H), 8.70 (s, 1 H), 8.17 (s, 1 H), 8.03 (d, J=7.2 Hz, 2 H), 7.61–7.40 (m, 5 H), 7.33–7.22 (m and overlapping d, J=8.7 Hz, 7 H), 6.82 (d, J=8.7 Hz, 4 H), 6.14 (d, J=7.2 Hz, 1 H), 5.25–5.13 (m and overlapping septet, J=6.3 Hz, 2 H), 4.91 (dd, J=7.2, 4.5 Hz, 1 H), 4.38 (d, J=1.5 Hz, 1 H), 3.78 (s, 6 H), 3.55 (dd, J=10.8, 3.6 Hz, 1 H), 3.50 (s, 3 H) 3.37 (dd, J=10.8, 3.6 Hz, 1 H), 1.79 (d, J=18.6 Hz, 3 H); $^{31}$P NMR (121 MHz, CDCl$_3$) δ35.05; HRMS (FAB$^+$) calcd for C$_{43}$H$_{40}$F$_6$N$_5$O$_9$P+H 916.2546, found 916.2570.

EXAMPLE 4

Preparation of Rp)- and (Sp)-1,1,1,3,3,3-Hexafluoro-2-propyl N$^2$-isobutyryl-5'-O-(4,4'-dimethoxytrityl)-2'-O-methylquanosine 3'-Methylphosphonate(6a,b, FIG. 3)

Following the general procedure of Example 2 with 47.86 g (58.7 mmol) of phosphoramidite 2 provided a 1:2.9 mixture (determined by HPLC integration) of diastereomers 6a (Sp, fast) and 6b (Rp, slow), respectively. Flash chromatography on silica gel using 6:1 methylene chloride-acetone gave 8.6 g (16%) of 6a, 15.7 g (30%) of 6b and 8.4 g (16%) of a mixture of 6a and 6b.

Diastereomer 6a: Rf 0.32 (5:2 methylene chloride-acetone); $^1$H NMR (300 MHz, CDCl$_3$) δ11.99 (s, 1 H), 8.77 (br s, 1 H), 7.79 (s, 1 H), 7.41–7.20 (m, 9 H), 6.76 (m, 4 H), 5.92–5.86 (dd, J=9.3, 4.5 Hz and overlapping d, J=5.1 Hz, 2 H), 5.24 (septet, J=5.7 Hz, 1 H), 4.89 (t, J=4.8 Hz, 1 H), 4.41 (m, 1 H),3.76 (s, 6 H), 3.55 (dd, J=11.1,1.8 Hz, 1 H), 3.48 (s, 3 H), 3.13 (dd, J=11.1, 2.7 Hz, 1 H), 1.98 (septet, J=6.6 Hz, 1 H), 1.65 (d, J=18.0 Hz, 3 H), 1.01 (d, J=6.9 Hz, 3 H), 0.87 (d, J=6.9 Hz, 3 H); $^{31}$p NMR (121 MHz, CDCl$_3$) δ35.01; HRMS (FAB$^+$) calcd for C$_{40}$H$_{42}$F$_6$N$_5$O$_{10}$P+H 898.2652, found 898.2675.

Diastereomer 6b: Rf 0.21 (5:2 methylene chloride-acetone); $^1$H NMR (300 MHz, CDCl$_3$) δ12.00 (s, 1 H), 7.85 (s, 1 H), 7.80 (s, 1 H), 7.52 (d, J=6.0 Hz, 2 H), 7.38 (d, J=9.0 Hz, 4 H), 7.27–7.13 (m, 3 H), 6.79 (app t, J=9.0 Hz, 4 H), 5.79 (d, J=7.5 Hz, 1 H), 5.36 (dd, J=9.0, 6.0 Hz, 1 H), 5.14 (m, 2 H), 4.28 (s, 1 H), 3.75 (s, 6 H), 3.54 (m, 1 H and overlapping s, 3 H), 3.06 (dd, J=11.1, 2.7 Hz, 1 H), 1.75 (d, J=18.6 Hz, 3 H), 1.54 (septet, J=6.6 Hz, 1 H), 0.88 (d, J=6.9 Hz, 3 H), 0.67 (d, J=6.9 Hz, 3 H); $^{31}$P NMR (121 MHz, CDCl$_3$) δ34.88; HRMS (FAB$^+$) calcd for C$_{40}$H$_{42}$F$_6$N$_5$O$_{10}$P+H 898.2652, found 898.2673.

EXAMPLE 5

Preparation of (Rp)- and (Sp)-1,1,1,3,3,3-Hexafluoro-2-propyl N$^4$-isobutyryl-5'-O-(4,4'-dimethoxytrityl)-2'-O-methylcytidine 3'-Methylphosphonate(7a,b, FIG. 3)

Following the general procedure of Example 2 with 58.0 g (74.8 mmol) of phosphoramidite 3 provided a 1:1.2 mixture (determined by HPLC integration) of diastereomers 7a (Sp, fast) and 7b (Rp, slow), respectively. Flash chromatography on silica gel using 6:1 methylene chloride-acetone gave 22.5 g (35%) of 7a, and 25.7 g (40%) of 7b.

Diastereomer 7a: Rf 0.42 (5:2 methylene chloride-acetone); $^1$H NMR (300 MHz, CDCl$_3$) δ9.41 (br s, 1 H), 8.50 (d, J=7.5 Hz, 1 H), 7.44–7.27 (m, 9 H), 7.09 (d, J=7.5 Hz, 1 H), 6.87 (d, J=8.7 Hz, 4 H), 6.01 (s, 1 H), 5.85 (m, 1 H), 5.24 (ddd, J=9.3, 9.3, 4.5 Hz, 1 H), 4.37 Hz, 1 H), 4.37 (d, J=8.7 Hz, 1 H), 4.30 (d, J=4.5 Hz, 1 H), 3.84 (s, 6 H), 3.70 (m, 1 H and overlapping s, 3 H), 3.41 (d, J=10.5 Hz, 1 H), 2.54 (septet, J=6.9 Hz, 1 H), 1.48 (d, J=18.3 Hz, 3 H), 1.15 (d, J=6.9 Hz, 3 H), 0.97 (d, J=6.9 Hz, 3 H); $^{31}$P NMR (121 MHz, CDCl$_3$) δ33.73; HRMS (FAB$^+$) calcd for C$_{39}$H$_{42}$F$_6$N$_3$O$_{10}$P+Cs 990.1566, found 990.1525.

Diastereomer 7b: Rf 0.21 (5:2 methylene chloride-acetone); $^1$H NMR (300 MHz, CDCl$_3$) δ9.17 (br s, 1 H), 8.45 (d, J=7.5 Hz, 1 H), 7.40–7.27 (m, 9 H), 7.07 (d, J=7.5 Hz, 1 H), 6.86 (d, J=8.7 Hz, 4 H), 6.08 (d, J=1.8 Hz, 1 H), 5.10–4.98 (m, 2 H), 4.35–4.29 (m, 2 H), 3.83 (2s, 6 H), 3.72 (s, 3 H), 3.67 (dd, J=11.4, 2.0 Hz, 1 H), 3.43 (dd, J=11.4, 2.0 Hz, 1 H), 2.57 (septet, J=6.9 Hz, 1 H), 1.86 (d, J=18.6 Hz, 3 H), 1.17 (d, J=6.9 Hz, 3 H), 1.04 (d, J=6.9 Hz, 3 H); $^{31}$P NMR (121 MHz, CDCl$_3$) δ36.00; HRMS (FAB$^+$) calcd for C$_{39}$H$_{42}$F$_6$N$_3$O$_{10}$P+Cs 990.1566, found 990.1607.

EXAMPLE 6

Preparation of (Rp)- and (Sp)-1,1,1,3,3,3-Hexafluoro-2-propyl 5'-O-(4,4'-dimethoxytrityl)-2'-O-methyluridine 3'-Methylphosphonate(8a,b, FIG. 3)

Following the general procedure of Example 2 with 25.21 g (35.7 mmol) of phosphoramidite 4 provided a 1:1.6 mixture (determined by HPLC integration) of diastereomers 3a (Sp, fast) and 8b. (Rp, slow), respectively. Flash chromatography on silica gel using 6:1 methylene chloride-acetone gave 8.7 g (31%) of 8a, and 14.0 g (49%) of 8b.

Diastereomer 8a: Rf 0.26 (6:1 methylene chloride-acetone); $^1$H NMR (300 MHz, CDCl$_3$) δ9.21 (br s, 1 H), 7.85 (d, J=8.1 Hz, 1 H), 7.37–7.25 (m, 9 H), 6.85 (d, J=8.7 Hz, 4 H), 6.07 (d, J=3.9 Hz, 1 H), 5.38 (septet, J=6.0 Hz, 1 H), 5.27 (d, J=8.1 Hz, 1 H), 5.15 (dt, J=8.4, 5.1 Hz, 1 H), 4.35 (t, J=6.9 Hz, 1 H), 4.03 (t, J=7.5 Hz, 1 H), 3.80 (s, 6 H), 3.61–3.55 (m, 1 H and overlapping s, 3 H), 3.46 (dd, J=11.1, 1.8 Hz, 1 H), 1.62 (d, J=18.0 Hz, 3 H); $^{31}$P NMR (121 MHz, CDCl$_3$) δ34.53; HRMS (FAB$^+$) calcd for C$_{35}$H$_{35}$F$_6$N$_2$O$_{10}$P+Cs 921.0988, found 921.1011.

Diastereomer 8b: Rf 0.17 (6:1 methylene chloride-acetone); $^1$H NMR (300 MHz, CDCl$_3$) δ9.59 (br s, 1 H), 7.81 (d, J=8.1 Hz, 1 H), 7.37–7.23 (m, 9 H), 6.85 (d, J=8.4 Hz, 4 H), 6.08 (d, J=4.5 Hz, 1 H), 5.38–5.26 (septet, J=6.0 Hz, 1 H and overlapping d, J=8.1 Hz, 1 H), 5.06 (dd, J=11.4, 5.1 Hz, 1 H), 4.24 (m, 1 H), 4.11 (t, J=4.8 Hz, 1 H), 3.80 (s, 6 H), 3.60–3.56 (s, 3 H and overlapping m, 1 H), 3.42 (dd, J=11.1, 1.8 Hz, 1 H), 1.75 (d, J=18.6 Hz, 3 H); $^{31}$P NMR (121 MHz, CDCl$_3$) δ35.20; HRMS (FAB$^+$) calcd for C$_{35}$H$_{35}$F$_6$N$_2$O$_{10}$P+Cs 921.0988, found 921.0952.

EXAMPLE 7

General Procedure for the Synthesis of 2'-OMe Methylphosphonate Dinucleotides

A solution of the 2'-OMe nucleoside-5'-OH component (ca. 2.0 g depending on dimer, 1.0 equivalent) in THF (15 mL) was dried over 3 Å molecular sieves at 50° C. (oil bath) under a positive pressure of argon for 12 hours prior to reaction. A solution of the 2'-OMe nucleoside 3'-1,1,1,3,3,3-hexafluoro-2-propyl methylphosphonate component (4.0 g, 1.2 equiv.) in THF (15 mL) was dried over 3 Å molecular sieves at room temperature under a positive pressure of argon for 12 hours prior to reaction. A flame-dried 100 mL one-neck round-bottomed flask was charged with tert-butylmagnesium chloride (1.0M solution in THF; 5.9 equivalents for GG; 4.9 equivalents for GC, GU and GA; 4.7 equivalents for AG, CG and UG; and 3.7 equivalents for all other dimers) via syringe. The solution was cooled to 0° C. (ice-water bath) and then 3-ethyl-3-pentanol was added (5.9 equivalents for GG; 4.9 equivalents for GC, GU and GA; 4.7 equivalents for AG, CG and UG; and 3.7 equivalents for all other dimers) via syringe. The resulting mixture was warmed to room temperature over 20 minutes to give a grey suspension. To this suspension was added via syringe the pre-dried THF solution of the 2'-OMe nucleoside 5'-OH component. The molecular sieves were rinsed with THF (2×4 mL) and the washings were added to the reaction flask. The yellow reaction mixture was stirred at room temperature for 20 minutes. Then the pre-dried THF solution of the 2'-OMe nucleoside 3'-1,1,1,3,3,3-hexafluoro-2-propyl methylphosphonate component was added via syringe. The molecular sieves were washed with THF (2×4 mL) and the washings were added to the reaction flask. The reaction flask was fitted with a condenser and then immersed in an oil bath which was pre-heated at 60°–65° C. The reaction was heated at this temperature under argon for 12–66 hours depending on the dimer. The reactions were quenched with saturated aqueous ammonium chloride solution and extracted with ethyl acetate (3×150 mL). Organic extracts were washed once with brine, dried ($MgSO_4$), filtered and concentrated under reduced pressure to give a yellow-orange foam. The crude product was purified by flash chromatography on silica gel (30 g silica gel/g of crude product) using 3:1 ethyl acetate-methylene chloride to elute excess 2'-OMe-nucleoside-5'-OH component and then 75:25:10 ethyl acetate-methylene chloride-methanol to elute the 2'-OMe dinucleoside-3'-OTBDPS derivative.

The 2'-OMe dinucleotide-3'-OTBDPS derivatives were desilylated by treatment with tetrabutylammonium fluoride (TBAF) reagent (1.0M in THF, 2.0 equiv.) at room temperature for 2 hours. The reaction mixtures were concentrated under reduced pressure to give a yellow foam, which was purified by flash chromatography on silica gel using a solvent mixture composed of 75:25:5 ethyl acetate-methylene chloride-methanol, gradually increasing to 75:25:15 ethyl acetate-methylene chloride-methanol to provide the 2'-OMe dinucleotide-3'-OH derivatives as pale yellow solids. Overall yields and spectral data for 2'-OMe dinucleotide-3'-OH compounds are shown in Table 4.

EXAMPLE 8

General Procedure for the Synthesis of 2',2"-bis (OMe) Methylohosphonates Dinucleoside Phosphoramidites Into a 100 ml one-neck round-bottomed flask was placed the 2'-OMe dinucleoside component (0.5–2.0 g depending on availability of dimer, 1.0 equivalent) and rendered anhydrous with pyridine co-evaporations (3×15 mls) on the roto-evaporator. The resulting solid foam was released from the roto-evaporator with argon then taken up in an appropriate volume of acetonitrile to give a 10% solution. While maintaining a positive argon pressure and with magnetic stirring was added triethylamine (2.5 equivalent) and 2'-Cyanoethyl-N,N-diisopropyl chlorophosphoramidite (1.5–2.0 equivalent) via syringe. The reactions proceeded at room temperature for 4 to 16 hours with the purine analogs generally requiring the longest time and the pyrimidine analogs the least amount of time. The reactions were monitored by HPLC, and if the reactions were not complete, then additional chlorophosphoramite was added. The reactions were concentrated to a thick slurry on a roto-evaporator then released under argon and dissolved in a minimum volume of ethyl acetate-methylene chloride-acetonitrile (3:1:1) and purified by flash chromatography on silica gel (10 g silica gel/g of crude product) with this same solvent mixture. The pure fractions were pooled and concentrated to a light yellow solid foam to produce the desired 2'-OMe methylphosphonate dinucleotide phosphoramidites.

EXAMPLE 9

Preparation of a Chirally Pure MP/MP Dimer Synthon

A CT-3'-OH dimer, 5.5 g (6 mM), was rendered anhydrous with two co-evaporations with pyridine. The resulting solid foam was released from the rotary evaporator with argon and stoppered with a rubber septa. The solid foam was dissolved in 100 ml of 9/1, $ACN/CH_2Cl_2$, then treated with 1.7 ml triethylamine (TEA, 12 mM). With magnetic stirring, the reaction mix was treated dropwise at room temperature with 1.5 ml chloromethyl-N,N-diisopropylamino phosphine (Cl-MAP, 8 mM). The reaction was monitored on HPLC (ACNMETH) and after 1.5 hours was complete, showing two main products, one at 3.5 minutes which was pyridine and a second at 14.3 minutes which was the desired amidite.

The reaction mixture was concentrated on a rotary evaporator using a partial vacuum; the flask which contained the resulting light amber sludge was released under argon and capped. The crude product was immediately passed through a flash column containing 60 grams of silica (first equilibrated in 1/1/1 $ACN/EtOAc/CH_2Cl_2$ with 3% TEA). The product was eluted quickly with this eluent and all U.V. positive fractions were pooled and concentrated. The resulting solid foam was co-evaporated with ACN to remove any residual TEA, then dried overnight under full vacuum. The final product, an off white solid foam, weight 5.0 grams.

EXAMPLE 10

Preparation of a Chirally Pure (CT) MP/DE Dimer Synthon

Into a 100 ml round bottom flask was placed 0.5 g (0.55 mMol) CT-3'-OH dimer which was rendered anhydrous by 3×20 ml co-evaporations with pyridine. The flask was released from the vacuum system under argon gas and stoppered with a rubber septa. The compound was redissolved in 10 ml acetonitrile and 200 μl (1.4 mMol, 2.5 eq) TEA were added. To the resulting mixture at room temperature and with manual stirring, was added in one portion 200 μl (0.90 mmol, 1.6 eq.) 2'-cyanoethyl-N,N-diisoprophylchlorophosphoramidite. The reaction mixture was allowed to sit at room temperature before being analyzed by reverse phase HPLC. The HPLC (Beckman System Gold, C18 bondapak, ACN method Solution A was 50/50 ACN/0.1M TEAA in water, pH 7 and Solution B was ACN. A gradient of 0 to 100% Solution B was run at a rate of 1 ml/minute over 25 minutes) showed complete conversion of starting material and a crude purity of greater than 90 percent. The diastereomers of the phosphoramidite were not resolved. The reaction mixture was concentrated under vacuum to a light yell solid foam. The foam was purified immediately by chromatography on 20 g of normal flash grade silica equilibrated with 5/1/5 ethyl acetate/acetonitrile/methylene chloride with 2% TEA to give 0.5 g (82% yield) of the above-identified product as an off-which solid foam having a purity of 99.3% as determined by HPLC.

EXAMPLE 11

Preparation of Chirally Pure CU MP(Rp) 2'-O-Methyl/MP 2'-O-Methyl Dimer Synthon Into a 100 ml round bottom flask was placed 400 mg (0.372 mmole) of 2'-O methyl CU dimer it was rendered anhydrous by 1×5 ml co-evaporation with acetonitrile. The dry foam was then released from the vacuum system under argon gas, dissolved in 4 ml ACN and stoppered with a rubber septa. The solution was treated with 2 equivalents TEA (103 μl, 0.744 mmol), followed by 1.75 equivalents chloro-methyl-N,N-diisopropyl phosphine ("Cl-MAP") (118 μl, 0.651 mmol). The reaction mixture was stirred for 1 hour at room temperature, after which time HPLC showed about 50/50 starting material/product. An additional 50 µl TEA and 70 µl Cl-MAP were then added and the mixture stirred for an hour. When HPLC showed only 80% conversion, an additional 30 µl TEA and 30 µl Cl-MAP were added and the resulting mixture stirred another hour. At this time HPLC revealed 6% starting material. The reaction mixture was concentrated to dryness. The residue was dissolved in 500 ml 3/1/3 ethylacetate/acetonitrile/methylene chloride with 4% TEA and loaded onto 5 g silica equilibrated in the same solvent system. Fractions were collected. The early fractions were contaminated with a yellow impurity and, thus, were pooled and concentrated separately. The product from those fractions was then repurified by chromatography using the same conditions and pooled with the clean product isolated from the first column. The combined products were co-evaporated with ACN (3×5 ml) and dried overnight under full vacuum to give 350 mg (77% yield) of the above identified product which HPLC showed to be 95.5% pure.

EXAMPLE 12

Preparation of a Chirally Pure 2'-O-Methyl MP 2'-O-Methyl/DE Dimer Synthon

A 230 mg portion of 2'-O-methyl CU 3'-OH dimer was rendered anhydrous by 2×5 ml co-evaporations in ACN. The resulting dry solid foam was dissolved in 2.5 ml ACN and then 73 µl (2.5 eq.) triethylamine ("TEA") and 94 µl (2.0 eq.) 2'-cyanoethyl-N,N-diisopropyl chlorophosphoramidite (βCNE) were added. The reaction mixture was stirred at room temperature for 2 hours at which time HPLC analysis determined the reaction to be complete. The reaction mixture was dissolved in eluent (3/1/1 ethylacetate/acetonitrile/methylene chloride with 4% TEA) and loaded onto 2 g silica gel equilibrated with 3/1/1 ethylacetate/acetonitrile/methylene chloride with 4% TEA. The column was run using 3/1/1 ethylacetate/acetonitrie/methylene chloride with 1% TEA. The clean fractions, 3 to 25, were concentrated, redissolved in acetonitrile and concentrated again to a solid foam. The foam was dried overnight under full vacuum to give 200 mg of the above-identified product.

EXAMPLE 13

Preparation of (Rp) N⁴-isobutyryl-5'-O-(4,4'-dimethoxytrityl)-2'-O-methylcytidine 2'-Methylphosphonate-5'-N⁴-isobutryrl-2'-O-methylcytidine Dinucleoside-3'-O-2'-Cyanoethyl-N,N-diisopropyl Phosphoramidine Following the proceduere of Example 8 with 2.50 g (2.49 mmol) of 2'-OMe dinucleoside 3'-OH (where $B_1$ is cytosyl) and 76 ul (5.48 mmol, 2.2 equivalent) of $Et_3N$ and 1.03 ml (4.60 mmol, 1.85 equivalent) of Cl-βCE showed 6% starting material by PHLC after stirring overnight at room temperature. Flash chromatography on 50 g of silica gel using 3:1:1 (ethyl acetate-methylene chloride-acetonitrile) gave 2.37 g (71.8%) of titled compound. $^{31}$P NMR (121 MHz, ACN-d3) δ35.798, δ153.038, 153.442.

TABLE 1

Comparison of methods for the stereospecific synthesis of 2',2"-bis(deoxy)methylphosphonate dinucleosides

| Dinucleo-side | Base/Metal System (Equivalents) | Rxn method[a] | Rxn time | Rp/Sp | Yield |
|---|---|---|---|---|---|
| AG | t-Butanol, DIBAL-H | A | 15 h | 0/0 | 0%[b] |
| AG | NaH, $ZnCl_2$ (5.0) | A | 70 h | 1/0 | 18%[b] |
| AG | t-Butoxy magnesium chloride (5.3) | A | 17 h | 1/0 | 76%[c] |
| AG | 3-Ethyl-3-pentanoxy magnesium chloride (5.0) | A | 17 h | 1/0 | 60%[b] |
| AG | Potassium hydride (4.5) | B | 0.5 h | 7.8/1 | ND |
| TT | Potassium hydride (4.5) | B | 0.5 h | 3/2 | ND |
| AG | Potassium t-butoxide (5.0) | A | 1 h | 4.3/1 | ND |
| TT | Potassium t-butoxide (5.0) | B | 1 h | 3/2 | ND |

[a]Method A: Reactions were run in THF at RT using 2:1 stoichiometry of 3'-phosphonate component:5'-OH component
Method B: Reactions were run in THF at RT using 1.3:1 stoichiometry of 3'-phosphonate component:5'-OH component
Method C: Reactions were run in THF at 50° C. using 1.3:1 stoichiometry of 3'-phosphonate component:5'-OH component
[b]Yield estimated by $^{31}$P NMR integration
[c]Yield of isolated product after purification
ND = not determined

TABLE 2

Results of the stereospecific synthesis of 2',2"-Bis(deoxy)methylphosphonate dinucleosides mediated by chloroalkoxy magnesium reagents

| Dinucleoside | Base/Metal System (Equivalents) | Rxn method[a] | Rxn time | Yield |
|---|---|---|---|---|
| AG | t-Butoxy magnesium chloride (5.3) | A | 17 h | 76%[c] |
| AG | 3-Ethyl-3-pentanoxy magnesium chloride (5.0) | A | 17 h | 60%[b] |
| AG | 3-Ethyl-3-pentanoxy magnesium chloride (4.5) | C | 4 h | 74%[b] |
| TC | 3-Ethyl-3-pentanoxy magnesium chloride (3.5) | B | 17 h | 18%[b] |
| TT | 3-Ethyl-3-pentanoxy magnesium chloride (3.5) | B | 17 h | 42%[b] |
| AT | 3-Ethyl-3-pentanoxy magnesium chloride (3.5) | C | 5 h | 55%[b] |
| CC | 3-Ethyl-3-pentanoxy magnesium chloride (3.2) | C | 4 h | 73%[b] |

[a]Method A: Reactions were run in THF at RT using 2:1 stoichiometry of 3'-phosphonate component:5'-OH component
Method B: Reactions were run in THF at RT using 1.3:1 stoichiometry of 3'-phosphonate component:5'-OH component
Method C: Reactions were run in THF at 50° C. using 1.3:1 stoichiometry of 3'-phosphonate component:5'-OH component
[b]Yield estimated by $^{31}$P NMR integration
[c]Yield of isolated product after purification

TABLE 3

Properties of 5'-DMT-2'-OMe methylphosphonate 1,1,1,3,3,3-hexafluoropropan-2-ol esters

| Compound | Ratio a(fast):b(slow) | Rf (a/b), method[c] | $^{31}$P NMR, δ (a/b)[d] |
|---|---|---|---|
| 5a,b | 1:2.8[a] | 0.27/0.18, B | 34.10/35.05 |
| 7a,b | 1:1.2[b] | 0.42/0.21, A | 33.73/36.00 |
| 6a,b | 1:2.9[b] | 0.32/0.21, A | 35.01/34.88 |
| 8a,b | 1:1.6[b] | 0.26/0.17, B | 34.53/35.20 |

TABLE 3-continued

Properties of 5'-DMT-2'-OMe methylphosphonate 1,1,1,3,3,3-hexafluoropropan-2-ol esters

| Compound | Ratio a(fast):b(slow) | Rf (a/b), method[c] | $^{31}$P NMR, δ (a/b)[d] |
|---|---|---|---|

[a]Determined by $^{31}$P integration of the crude product
[b]Determined by Reverse-phase HPLC of the crude product
[c]Method A: 5:2 methylene chloride-acetone on Silica gel 60 $F_{254}$ TLC plates
Method B: 6:1 methylene chloride-acetone on Silica Gel 60 $F_{254}$ TLC plates
[d]Relative to 85% $H_3PO4$

TABLE 4

Properties of 5'-O-DMT-3'-OH-2',2"-bis(OMe)methylphosphonate Dinucleosides

| 2'-OMe Dinucleoside | % Overall Yield | Purity (% Rp/ %Sp)[a] | $^{31}$P NMR, δ (Rp/Sp)[b] | Exact Mass (calc'd) | HRFAB+ MS, found (adduct) |
|---|---|---|---|---|---|
| AG | 42% | 98.0/ 0.2% | 31.70/ 33.41 | 1114.3949 | 1115.4077 (M + H)+ |
| AA | 32% | 90.0/ 9.0% | 31.77/ 33.50 | 1132.3843 | 1265.2935 (M + Cs)+ |
| AC | 64% | 97.4/ 2.2% | 31.44/ ND | 1074.3887 | 1207.2895 (M + Cs)+ |
| AU | 27% | 97.2/ 2.6% | 31.26/ 33.14 | 1005.3309 | 1138.2325 (M + Cs)+ |
| CG | 15% | 96.1/ 3.2% | 31.42/ ND | 1056.3993 | 1189.3094 (M + Cs)+ |
| CA | 22% | 89.1/ 6.5% | 32.27/ ND | 1074.3887 | 1207.2890 (M + Cs)+ |
| CC | 38% | 91.5/ 5.0% | 32.13/ 34.21 | 1016.3932 | 1149.2948 (M + Cs)+ |
| CU | 28% | 83.4/ 1.2% | 32.01/ ND | 947.3353 | 1080.2373 (M + Cs)+ |
| GG | 25% | 95.9/ 1.9% | 32.29/ ND | 1096.4054 | 1097.4156 (M + H)+ |
| GA | 39% | 95.8/ 2.9% | 32.40/ ND | 1114.3949 | 1247.3025 (M + Cs)+ |
| GC | 46% | 94.3/ 4.5% | 31.45/ 32.92 | 1056.3993 | 1057.4092 (M + H)+ |
| GU | 28% | 93.8/ 5.6% | 32.37/ 33.22 | 987.3415 | 1010.3333 (M + Na)+ |
| UG | 15% | 88.0/ 11.5% | 31.54/ ND | 987.3415 | 1120.2429 (M + Cs)+ |
| UA | 40% | 92.0/ 6.8% | 32.21 ND | 1005.3309 | 1138.2328 (M + Cs)+ |
| UC | 26% | 89.0/ 11.0% | 31.93/ 33.13 | 947.3353 | 1080.2420 (M + Cs)+ |
| UU | 36% | 78.0/ 20.0% | 31.67/ ND | 878.2775 | 1011.1794 (M + Cs)+ |

[a]Determined by reverse-phase HPLC
[b]Relative to 85% $H_3PO_4$
ND = not determined

What is claimed is:

1. A process for the diastereospecific preparation of 2',2"-dideoxy-diribonucleotide phosphonates of the formula 1

(1)

wherein

T is a triphenylmethyl protecting group for a primary hydroxyl group;

$B_1$ and $B_2$ are independently selected deoxyribonucleoside bases and may be the same or different;

G is an acyl or silyl protecting group for a secondary hydroxyl group or a solid support;

Z is selected from the group consisting of oxygen, sulfur and selenium; and $R_1$ is selected from the group consisting of an alkyl moiety having 1 to 8 carbon atoms, cyclohexyl, benzyl, phenyl and phenyl substituted by a member selected from the group consisting of fluorine, chlorine, bromine, lower alkyl, lower alkoxy and trifluoromethyl, which comprises (a) reacting an alkylmagnesium halide, with a hindered tertiary alcohol, to give a halomagnesium alkoxide;

(b) reacting the halomagnesium alkoxide with an alcohol of formula 2

(2)

; and (c) subsequently adding a diastereomerically pure Rp- or Sp- compound of formula 3,

3 wherein E is an anion stabilizing group with leaving group properties to give the diastereomerically pure Sp-alkylphosphonate dinucleoside of formula 1 wherein stereochemistry at the phosphorus atom is inverted with respect to the stereochemistry of the configuration of the phosphorus atom of formula 3.

2. The process of claim 1 wherein said alkylmagnesium halide is t-butylmagnesium chloride.

3. A process according to claim 2 wherein said hindered tertiary alcohol is selected from t-butanol, 3-ethyl-3-pentanol or 1-adamanantol.

4. The process of to claim 1 wherein said hindered tertiary alcohol is selected from t-butanol, 3-ethyl-3-pentanol or 1-adamantanol.

5. The process of to claim 1 wherein E is selected from a lower perfluoroalkyl group of 1 to about 6 carbon atoms, an aryl group of 6 to about 10 carbon atoms substituted with 1 to about 2 electron withdrawing substituents or n-succinimidyl.

6. The process of claim 5 wherein E is selected from 1,1,1,3,3,3-hexafluoro-2-propyl, 4-nitrophenyl or N-succinimidyl.

7. The process of claim 6, wherein

T is selected from the group consisting of triphenylmethyl, p-anisoylphenylmethyl and di(p-anisoyl)phenylmethyl, and $R_1$ is selected from the group consisting of methyl, ethyl, phenyl, benzyl and propynyl.

8. The process of claim 1, wherein the compounds of formulas 2 and 3 are reacted at about −80° to about 100° C.

9. The process of claim 6, wherein the reaction takes place at about 0° to about 30° C.

10. A process for the diastereoselective preparation of 2',2"-bis(substituted)diribonucleotide phosphonates of the formula 4 wherein

T is a triphenylmethyl protecting group for a primary hydroxyl group; $B_1$ and $B_2$ are independently selected nucleoside bases and may be the same or different; G is an acyl or silyl protecting group for a secondary hydroxyl group or a solid support; Z is selected from the group consisting of oxygen, sulfur and selenium; $R_1$ is selected from the group consisting of an alkyl moiety having 1 to 8 carbon atoms, cyclohexyl, benzyl, phenyl and phenyl substituted by a member selected from the group consisting of lower alkyl and trifluoromethyl; and $R_2$ is selected from the group consisting of hydrogen, O-alkyl of 1 to about 10 carbon atoms, O-alkenyl, O-aralkyl of 7 to about 11 carbon atoms, O-aryl of 6 to about 10 carbon atoms, halogen and nitrile; which comprises:

(a) reacting an alkylmagnesium halide, with a hindered tertiary alcohol to give a halomagnesium alkoxide;

(b) reacting the halomagnesium alkoxide of step (a) with an alcohol of formula 5 and (c) subsequently adding a diastereomerically pure Rp- or Sp- compound of formula 6, wherein E is an anion stabilizing group with leaving group properties to give the diastereomerically-enriched alkylphosphonate dinucleoside of formula 4, and wherein inversion of stereochemistry at the phosphorus atom of formula 6 is favored.

11. The process of claim 10 wherein said alkylmagnesium halide is t-butylmagnesium chloride.

12. The process of to claim 11 wherein said hindered tertiary alcohol is selected from t-butanol; 3-ethyl-3-pentanol or 1-adamanantol.

13. The process of claim 10 wherein said hindered tertiary alcohol is selected from t-butanol, 3-ethyl-3-pentanol or 1-adamantanol.

14. The process of claim 10 wherein E is selected from a lower perfluoroalkyl group of 1 to about 6 carbon atoms, an aryl group of 6 to about 10 carbon atoms substituted with 1 to about 2 electron withdrawing substituents, or N-succinimidyl.

15. The process of claim 14 wherein E is selected from 1,1,1,3,3,3-hexafluoro-2-propyl, 4-nitrophenyl or N-succinimidyl.

16. The process of claim 14 wherein $R_2$ is selected from O-lower alkyl, O-allyl, O-phenyl, O-benzyl, halogen or nitrile.

17. The process of claim 16 wherein

T is selected from the group consisting of triphenylmethyl, p-anisoyldiphenylmethyl and di(p-anisoyl)phenylmethyl, and $R_1$ is selected from the group consisting of methyl, ethyl, phenyl, benzyl and propynyl.

18. The process of claim 10, wherein the compounds of formula 5 and 6 are reacted at a temperature of about 15° C. to about 65° C.

19. The process of claim 18, wherein the reaction takes place at about 50° C. to about 60° C.

20. A compound of a formula 4 wherein T is selected from the group consisting of triphenylmethyl, p-anisoyldiphenylmethyl and di(p-anisoyl)phenylmethyl; $B_1$ and $B_2$ are independently selected nucleoside bases and are the same or different; $R_1$ is selected from the group consisting of methyl, ethyl, phenyl, benzyl and propynyl; $R_2$ is selected from the group consisting of O-alkyl of 1 to about 10 carbon atoms, O-alkenyl of 2 to about 10 carbon atoms, O-aralkyl of 7 to about 10 carbon atoms, O-aryl of 6 to about 10 carbon atoms, halogen and nitrile; and G is selected from the group consisting of t-butyl-dimethylsilyl, trimethylsilyl, t-butyl-diphenylsilyl, and a solid support which is diastereomerically pure at the phosphorus atom.

21. A process for the preparation of diastereomerically pure 2'-substituted nucleoside alkylphosphonate active esters of the formula 6:

wherein

T is a triphenylmethyl protecting group for a primary hydroxyl group; $B_1$ is a nucleoside base; G is an acyl or silyl protecting group for a secondary hydroxyl group or a solid support; Z is selected from the group consisting of oxygen, sulfur and selenium; $R_1$ is selected from the group consisting of an alkyl moiety having 1 to 8 carbon atoms, cyclohexyl, benzyl, phenyl and phenyl substituted by a member selected from the group consisting of lower alkyl and trifluoromethyl; and $R_2$ is selected from the group consisting of hydrogen, O-alkyl of 1 to about 10 carbon atoms, alkenyl of 2 to about 10 carbon atoms, O-aralkyl of 7 to about 11 carbon atoms, O-aryl of 6 to about 10 carbon atoms, halogen and nitrile; and E is an anion stabilizing group with leaving group properties; which comprises (a) reacting a phosphonamidite reagent of formula 7 with an alcohol of formula E-OH, in the presence of a weak organic acid in a polar aprotic solvent;

(b) oxidatively converting the P(III) intermediate to a compound of formula 6; and (c) chromatographically separating the mixture of Rp- and Sp- diastereomers formed in the reaction.

22. The process of to claim 21 wherein E is selected from a lower perfluoroalkyl group of 1 to about 6 carbon atoms, an aryl group of 6 to about 10 carbon atoms substituted with 1 to about 2 electron withdrawing substituents or N-succinimidyl.

23. The process of claim 22 wherein said weak organic acid is selected from tetrazole and 3-ethylthiotetrazole.

24. The process of claim 23 wherein said polar aprotic solvent is acetonitrile.

25. The process of claim 24 wherein said anion stabilizing group is 1,1,1,3,3,3-hexafluoro-2-propyl; 4 nitrophenyl or N-succinimidyl.

26. A compound of formula 6 wherein

T is a triphenylmethyl protecting group for a primary hydroxyl group; $B_1$ is a nucleoside base; Z is selected from oxygen, sulfur or selenium; $R_1$ is selected from the group consisting of methyl, ethyl, phenyl, benzyl and propenyl; $R_2$ is selected from the group consisting of hydrogen, O-alkyl of 1 to about 10 carbon atoms, O-alkenyl of 1 to about 10 carbon atoms, O-aralkyl of 7 to about 10 carbon atoms, O-aryl of 6 to about 10 carbon atoms, halogen and nitrile; and E is an anion stabilizing group with leaving group properties.

27. A compound according to claim 26 which is the Rp diastereomer.

28. A compound according to claim 26 which is the Sp diastereomer.

29. A compound according to claim 26 wherein E is selected from a lower perfluoroalkyl group of 1 to about 6 carbon, an aryl group of 6 to about 10 carbon atoms substituted with 1 to about 2 electron withdrawing substituents and or N-succinnimidyl.

30. A compound according to claim 29 wherein E is 1,1,1,3,3,3-hexafluoro-2-propyl, 4-nitrophenyl or N-succinimidyl.

* * * * *